United States Patent
Arai

[19]

[11] Patent Number: 6,095,949
[45] Date of Patent: Aug. 1, 2000

[54] HEALTH MANAGEMENT DEVICE

[75] Inventor: Kazuo Arai, Ageo, Japan

[73] Assignee: ADK Corporation, Saitama, Japan

[21] Appl. No.: 09/099,516

[22] Filed: Jun. 17, 1998

[30] Foreign Application Priority Data

Jun. 18, 1997 [JP] Japan .................................. 9-161546

[51] Int. Cl.⁷ ................................................. G06F 19/00
[52] U.S. Cl. ............................................. 482/4; 434/127
[58] Field of Search ................... 482/1–9, 57, 900–902; 434/127

[56] References Cited

U.S. PATENT DOCUMENTS

| | | | |
|---|---|---|---|
| 4,192,000 | 3/1980 | Lipsey | 482/8 |
| 5,640,774 | 6/1997 | Goldman | 434/127 |
| 5,839,901 | 11/1998 | Karkanen | 434/127 |

FOREIGN PATENT DOCUMENTS 8-103568  4/1996  Japan .

Primary Examiner—Glenn E. Richman

[57] ABSTRACT

A health management device according to this invention comprises: an exercise quantity measurer for measuring a quantity of exercise; an intake calorie calculator for calculating an intake calorie on the basis of input information of meal including the types and quantities of foods; a consumption calorie calculator for calculating, on the basis of the information of a quantity of exercise measured by the exercise quantity measurer, a calorie consumed by the exercise; a calorie balance analyzer for analyzing a calorie balance on the basis of the calculation results of the intake calorie and the consumption calorie; a diet effect simulator for simulating a diet effect on the basis of the information of the analyzed calorie balance and personal information; and a moving image display controller for changing a display character to display the diet effect with a moving image.

17 Claims, 7 Drawing Sheets

```
 1, BOILED RICE
 2, BREAD
 3, MILK
 4, VEGETABLE
 5, FRUIT
 6, FAST FOOD
 7, CONFECTIONERY
 8, SOMETHING TO DRINK
 9, EUROPEAN FOOD
10, CHINESE FOOD
11, JAPANESE-STYLE FOOD
12, SIDEDISH
13, OTHERS
```
— FD1

FIG.6A

```
1, BOILED-RICE TEACUP IS FULL   163KCAL
2, BOILED-RICE BOWL RICE BALL   444KCAL
3, RICE BALL                    158KCAL
4, RICE GRUEL                   144KCAL
```
— FD11

FIG.6B

```
 1, RAPID WALKING   38KCAL
 2, GOLF            34KCAL
 3, JAZZ DANCE      50KCAL
 4, SWIMMING       145KCAL
 5, SKIING          59KCAL
 6, BICYCLE         31KCAL
 7, BOWLING         26KCAL
 8, GYMNASTICS      38KCAL
 9, DANCE           34KCAL
10, VOLLEYBALL      59KCAL
11, WORK            20KCAL
12, OTHERS
```
— MD1

FIG.7

HEALTH MANAGEMENT DEVICE

BACKGROUND OF THE INVENTION

1. Field of the Invention

The present invention relates to a device for health management using a computer and, more particularly, to a health management device, having a simulation function of a diet effect or a health condition, for providing useful information for health management.

2. Description of the Related Art

In present society, dieting and coping with a lack of exercise cannot be achieved, and many persons get adult diseases because corpulent persons increase in number. It is currently said that a slim person has good proportions. Some persons may become mental diseases such as sitophobia and the like because of excessive dieting. Since many adult diseases are caused by a life habit such as an eating habit or exercise, the adult diseases may be called life-habit diseases. Although such a life-habit disease of a person can be cured by his/her efforts, even if a target is set to cope with a lack of exercise, it is very difficult to continue appropriate exercise. Some foods have ingredient tables printed on sheets of wrapping paper or vessels. However, highest efforts are required for the follows. That is, the ingredient tables are transferred to calculate an intake calorie everyday, and a lack/surplus of intake calorie is examined to adjust a quantity of food, thereby improving an eating habit. In addition, it is extremely difficult that the above operations are performed while considering a nutrition balance. For example, when exercise such as walking or swimming is performed for dieting or health, a person who has special knowledge can predict, in consideration of his/her present conditions and a quantity of intake food, that a specific quantity of exercise causes a specific degree of effect. However, a general person cannot easily perform the prediction.

As devices for health management used by general persons, weight scales or body fat range analyzers are conventionally known. As devices for measuring quantities of exercise, pedometers and indoor athletic tools having functions of measuring quantities of running an d quantities of exercise by bicycles are known. A general person measures his/her weight with a weight scale, measures his/her body fat range with a body fat range scale, or checks his/her proportions with a mirror to confirm a diet effect. Furthermore, it is confirmed by checking measurement values such as the number of steps and exercise time whether target exercise is performed or not.

However, in order to cope with a lack of exercise or improve an eating habit by using the above health management devices and indoor athletic tools, it is general that only few persons can continue these endeavors for a long time. A person who has special knowledge can predict, in consideration of his/her present conditions and a quantity of intake food, that a specific quantity of exercise causes a specific degree of effect. However, a general person cannot easily perform the prediction.

SUMMARY OF THE INVENTION

The present invention has been made in consideration of the above circumstance, and has as its object to provide a health management device in which a diet effect or a health condition is simulated to express the results with a moving image, an improvement of an eating habit or coping with a lack of exercise can be pleasantly achieved with the feeling of game, and information useful for health management can be provided.

The present invention relates to a device for health management using a computer, and the object of the present invention is effectively achieved by comprising exercise quantity measurement means for measuring a quantity of exercise; intake calorie calculation means for calculating an intake calorie on the basis of input information of meal including the types and quantities of foods; consumption calorie calculation means for calculating, on the basis of the information of a quantity of exercise measured by the exercise quantity measurement means, a calorie consumed by the exercise; calorie balance analysis means for analyzing a calorie balance on the basis of the calculation results of the intake calorie and the consumption calorie; diet effect simulation means for simulating a diet effect on the basis of the information of the analyzed calorie balance and personal information; and moving image display control means for changing a display character to display the diet effect with a moving image. In addition, when the arrangements according to claims 2 to 17 are employed, the object can be effectively achieved.

BRIEF DESCRIPTION OF THE DRAWINGS

In the accompanying drawings;

FIGS. 6A and 6B are tables showing food lists used in the present invention;

FIG. 7 is a table showing an exercise list used in the present invention; and

DESCRIPTION OF THE PREFERRED EMBODIMENT

According to the present invention, a display character is changed in proportion or action depending on a balance state between an intake calorie and a consumption calorie, or the character is changed depending on an unbalanced eating state, thereby expressing a diet effect or a health condition. In this case, an intake calorie in a meal is calculated on the basis of food information selectively designated from a food list, and a consumption calorie depending on a quantity of exercise is calculated on the basis of a measurement value of an exercise quantity measurer such as a pedometer. The device also comprises a function of calculating a consumption calorie on the basis of exercise information selectively designated from an exercise list. The device in this embodiment is realized such that a step count detector is built in a portable compact game machine, or a measurement information input means of a quantity of exercise is arranged in the game machine. The present invention can be applied to a device for health management, a diet simulation device, and a game machine in which a game is played while measurement information of a quantity of exercise is reflected on a game story.

A preferable embodiment of the present invention will be described below with reference to the accompanying drawings.

Figure 1:
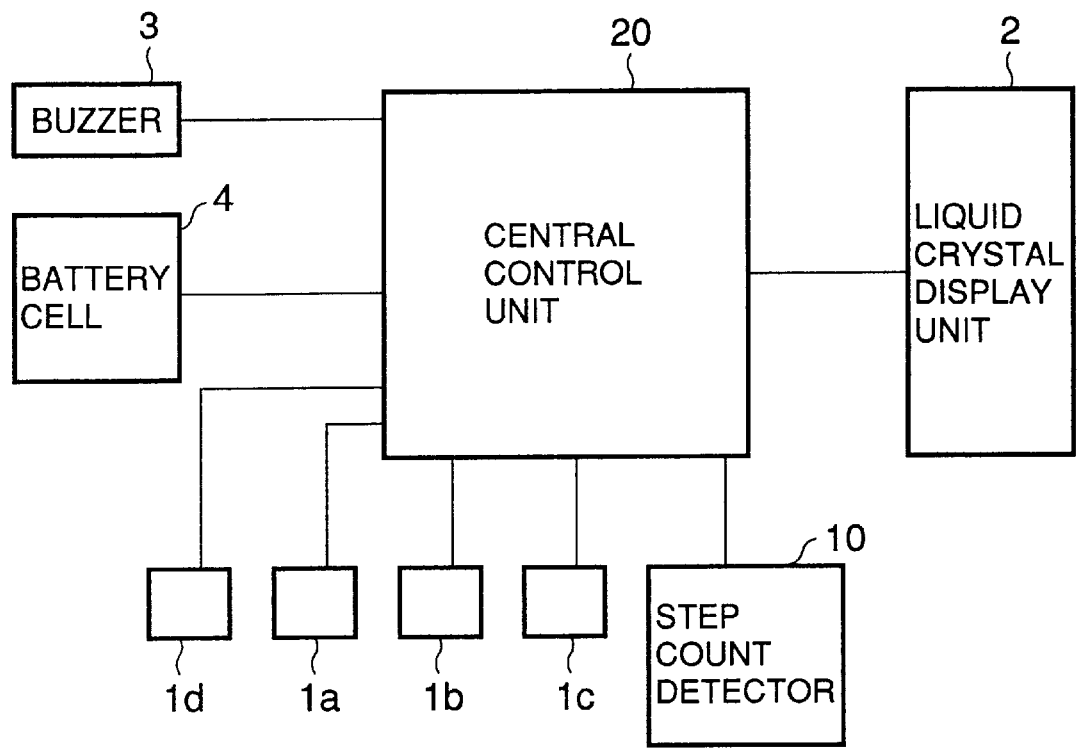
FIG. 1 is a block diagram showing a hardware arrangement of a portable health management device according to the present invention.
Figures 2A, 2B:
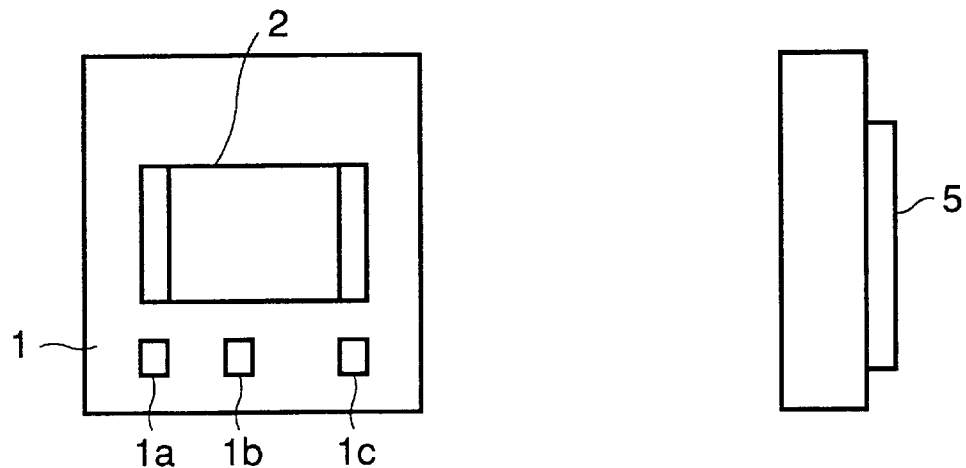
FIGS. 2A and 2B are a front view and a side view showing an outside arrangement of the device according to the present invention.

FIG. 1 is a block diagram showing a hardware arrangement of a portable health management device according to the present invention, and FIG. 2 is an outside arrangement of the health management device in FIG. 1. The size of housing is almost equal to that of a portable compact game machine (so-called minimum liquid-crystal game machine) using a computer. As shown in the front view in FIG. 2A, an operation unit 1 and a liquid-crystal display unit 2 are arranged on the front surface of the health management device. The operation unit 1 comprises a selection switch 1a for selecting various modes (to be described later), a determination switch 1b for fixing a selected candidate, a cancel switch 1c for canceling the fixed candidate, and a reset switch 1d (not shown). The health management device according to this embodiment incorporates a step count detector (step count detection switch) 10 for detecting a quantity of exercise by walking as an exercise quantity measurer for measuring a quantity of exercise of a holder. As shown in the side view in FIG. 2B, a hook 5 is integrally or detachably formed on the rear surface of the health management device, so that the health management device can be attached to a waist portion to be carried by a user.

In FIG. 1, the health management device comprises: a central control circuit 20 constituted by a micro CPU, a RAM, a ROM, an I/O interface, and the like for controlling execution of a health management program according to the present invention; an exercise quantity measurer (step count detector in this embodiment) 10 for measuring a consumption calorie consumed by exercise; switches 1a to 1d for the operation; a liquid-crystal display unit 2; and a buzzer 3. As a power supply, a battery cell (chemical battery cell, a solar battery cell, or the like) 4 is used. The health management device is always energized. A detection signal from the step count detector 10 is input to the central control circuit 20 such that a consumption calorie consumed by walking exercise can be automatically calculated on the basis of the detection signal.

The health management device has, as main functions, a function of calculating an intake calorie, a function of calculating a consumption calorie, a function of analyzing a calorie balance, a function of simulating a diet effect obtained by meal and exercise, a function of determining a health condition, and a function of displaying a diet effect or a health condition with a moving image like a game. A program for realizing these functions is recorded on a recording medium (the ROM in the central control circuit 20 in this embodiment).

Figure 3:
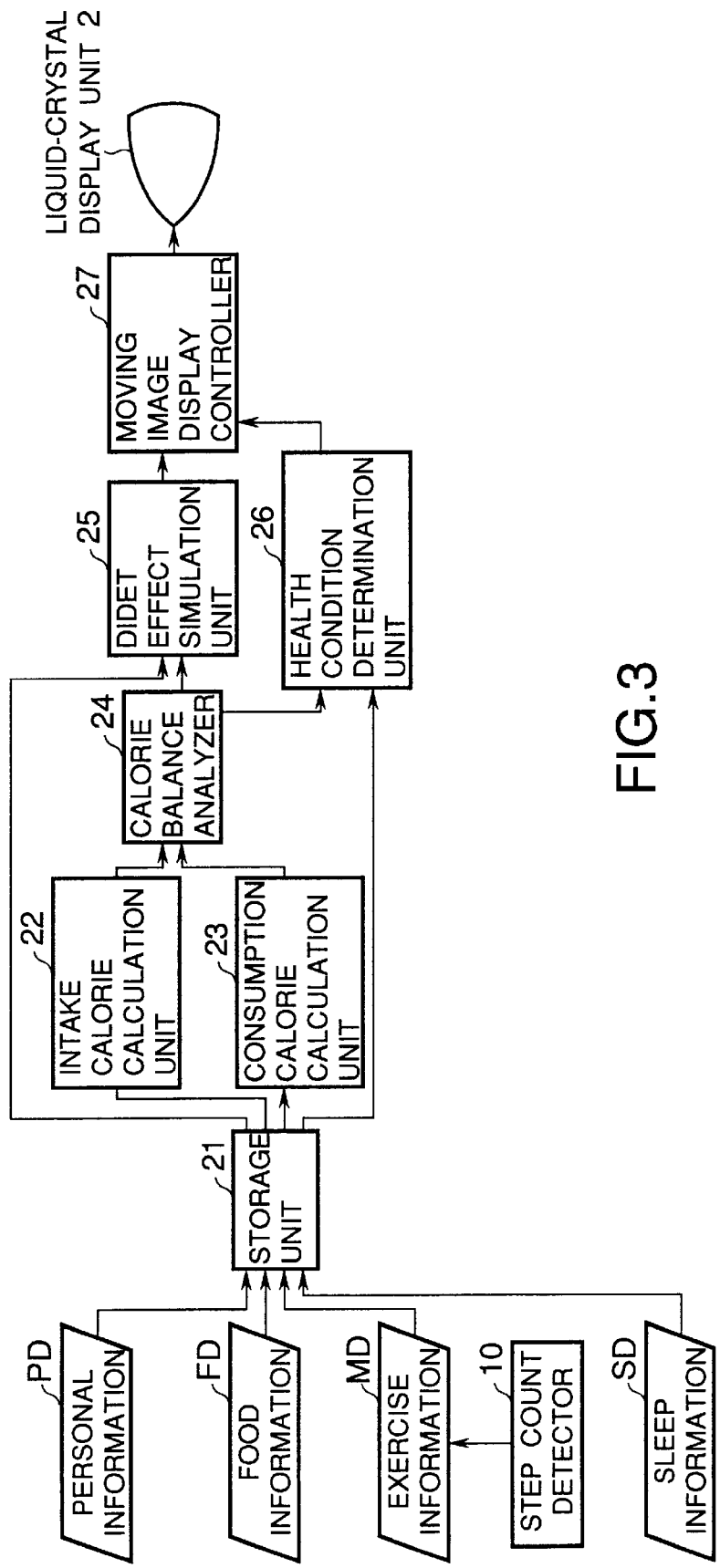
FIG. 3 is a block diagram of a functional arrangement of the device according to the present invention.

FIG. 3 is a block diagram showing a functional arrangement of the health management device. The main functions held by the health management device will be briefly described below with reference to FIG. 3.

As input information, personal information (height, weight, age, sex, and the like) PD, food information (type of food eaten by a person and the like) FD, exercise information (type of exercise, quantity of exercise, and the like) MD, and sleep information (bedtime, the hour of rising, and the like) SD are used. Exercise information MD obtained by walking is automatically input from the step count detector 10, and exercise information MD obtained by other exercise is input by a menu selection operation of the operation switch 1 like other pieces of information PD, FD, and SD to be stored in a storage unit 21.

In an intake calorie calculation unit 22, when the food information FD is input by operating the operation switch 1, an intake calorie obtained by a food (including a drink) is calculated on the basis of the food information FD. On the other hand, when the exercise information MD is input from the exercise quantity measurer 10 (or by operating the operation switch 1), a consumption calorie calculation unit 23 calculates a consumption calorie (quantity of active energy) consumed by exercise on the basis of the exercise information MD and the personal information PD. The calculated intake calorie and the calculated consumption calorie are stored in the storage unit 21, the sum of intake calories per day and the sum of consumption calories per day are calculated, respectively, to be stored. As the consumption calorie, a calorie (basal metabolic rate) consumed in a rest state and a calorie (food-inductive thermogenesis) consumed when a food is absorbed are added to each other.

In a calorie balance analyzer 24, a balance state between an intake calorie and a consumption calorie is analyzed. In this embodiment, the difference between the intake calorie and the consumption calorie is calculated, and the difference is set as a variable parameter Xa of (quantity of loss of weight)/(quantity of gain in weight). In a diet effect simulation unit 25, a diet effect obtained by a dieting method or an exercise method is simulated on the basis of the variable parameter Xa and the personal information PD. On the other hand, in a health condition determination unit 26, overeating, unbalanced eating, a lack of exercise, and the like are checked on the basis of an analysis result (variable parameter Xa) of a calorie balance, the food information FD, the exercise information MD, and the personal information PD to determine a health condition. For example, the degree of health of elements, and the degree of health as a whole is calculated on the basis of the sum of the degrees of health, so that the degree of health as a whole is displayed.

In a moving image display controller 27, a personified character or a pseudo creature character is changed in proportion or action on the basis of the analysis result of a calorie balance and the determination result of a health condition, so that a diet effect or a health condition is displayed on the liquid-crystal display unit 2 with a moving image.

Figure 4A:
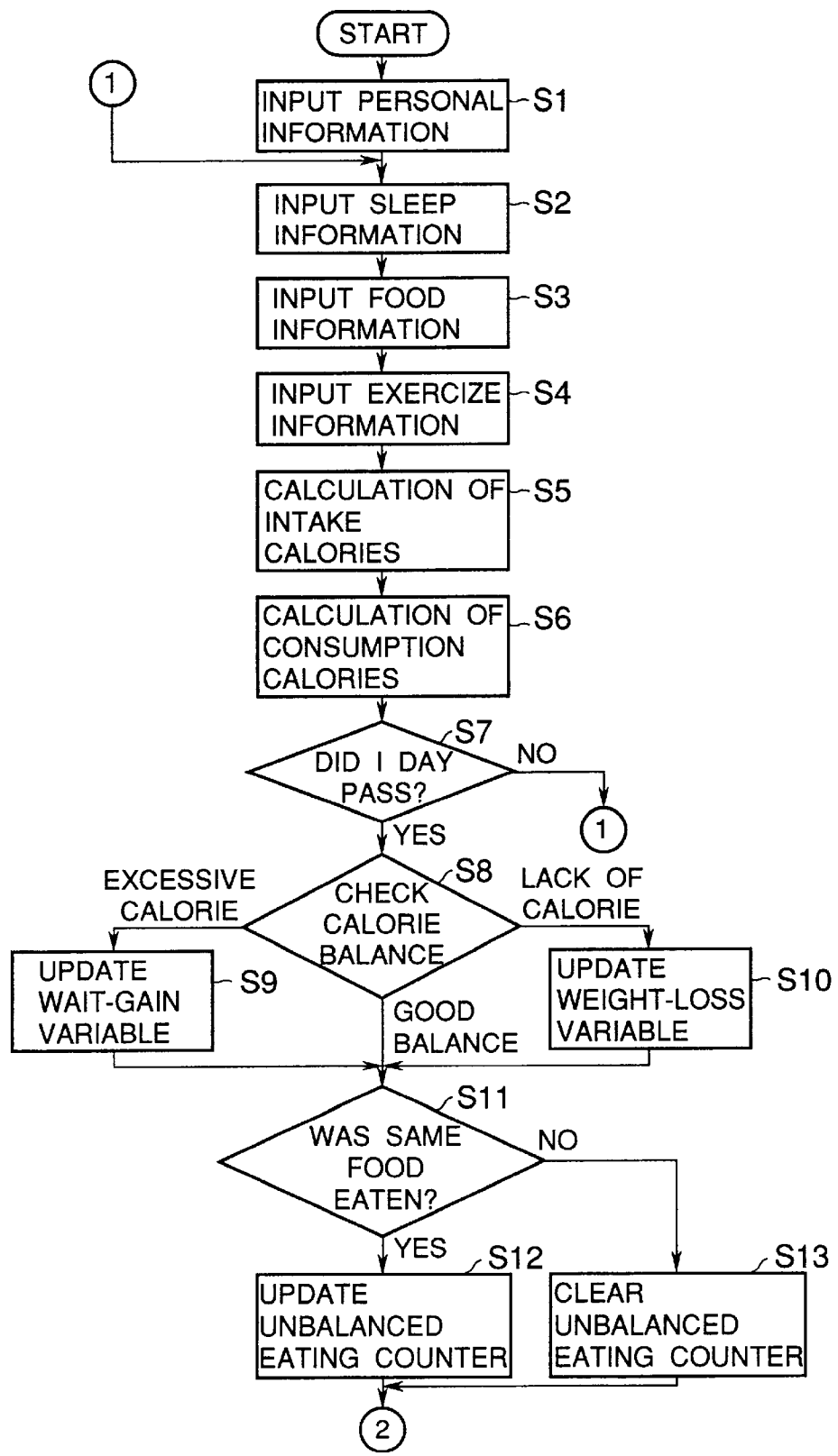
FIGS. 4A and 4B are flow charts for explaining operations of the device according to the present invention.
Figure 4B:
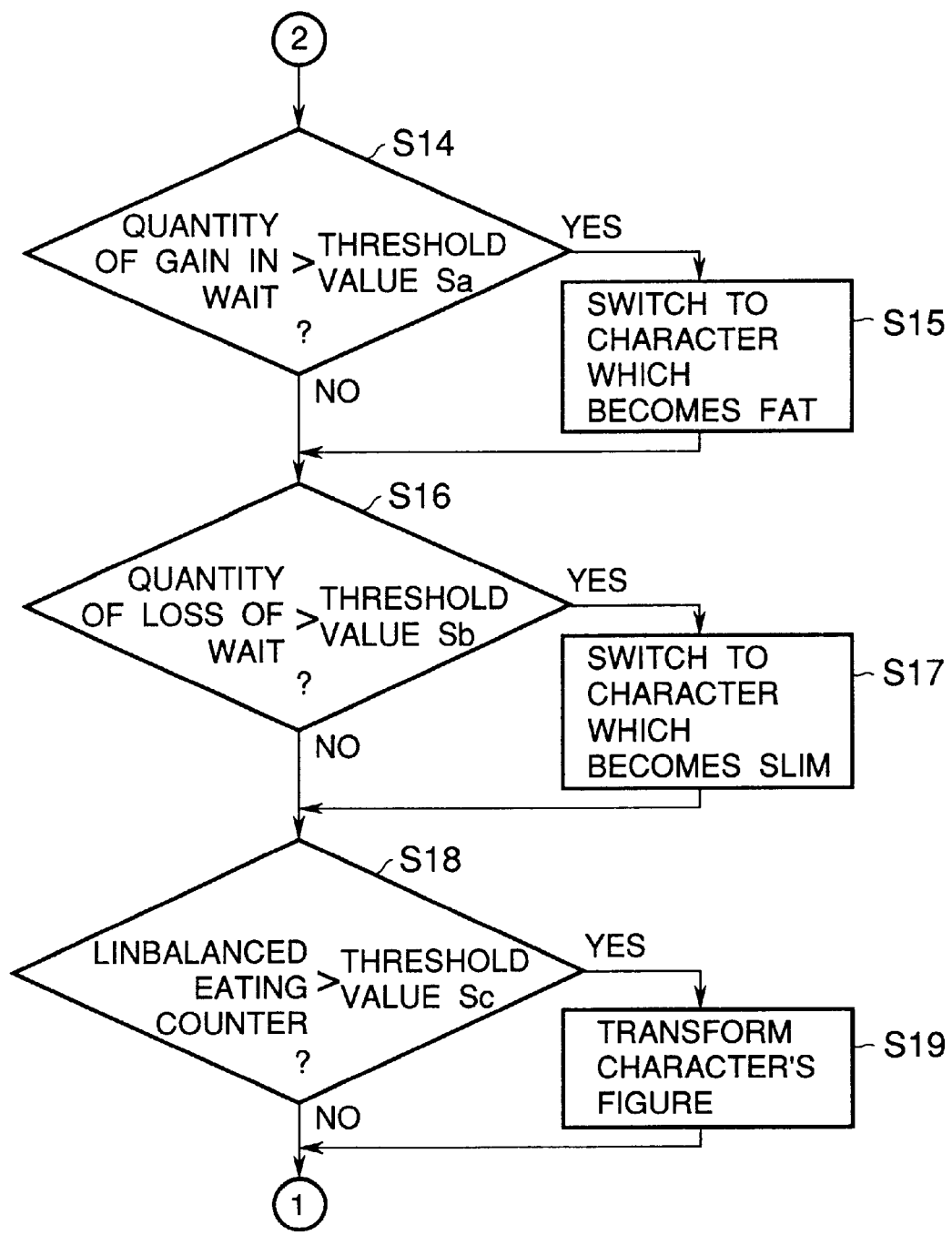
Figure 5A:
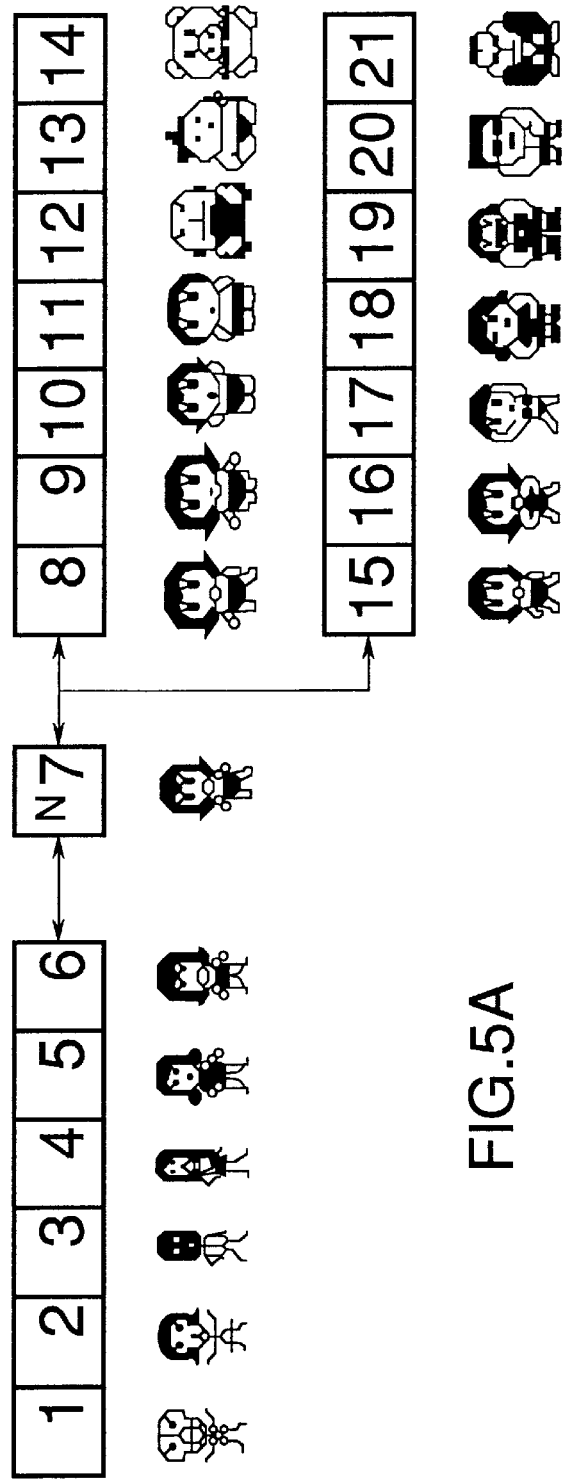
FIGS. 5A and 5B are view showing concrete examples of a display character.

In the above arrangement, operations and functions will be described in detail with reference to the flow charts in FIGS. 4A and 4B. First, a user (to be referred to as "a player" hereinafter) operates the selection switch 1a to select a registration mode of personal information, and registers the personal information PD. As the personal information, the weight of the player, target weight, height, age, sex, expected bedtime, expected hour of rising, and the like are input. Although the personal information is input only once, when the program is to be performed again from the beginning, the reset switch 1d is pressed to initialize the device. When the personal information is registered, the control mode is changed from a registration mode to an execution mode, and the character of a hero corresponding to the other self of the player is displayed on the liquid-crystal display unit 2 to start operation control for the character. For the character of the hero, as shown in FIG. 5A, characters on a plurality of stages are prepared such that a standard figure N7 is changed into slim figures (1 to 6), fat figures (8 to 14), or muscular figures (15 to 21). In the initial state of the character, a character having the standard figure N7 is designed to appear (Step S1). Subsequently, the player inputs the sleep information SD, the food information FD, and the exercise information MD in accordance with his/her behavior.

Here, main commands in the execution mode will be described below. In the execution mode, commands (to be referred to as "mode" hereinafter) "meal", "exercise", "sleeping", "rising", and "situation observation" are set. In the execution mode, a player selects one of the modes "meal", "exercise", "sleeping", and "rising". When the player wants to observe a present situation, the player selects the mode "situation observation" to inquire information such as a walking distance, an intake calorie, a weight, or the degree of health.

The modes "sleeping"and "rising" are modes for inputting the sleep information SD (bedtime and the hour of rising). The player selects each of the modes when he/she goes to bed and wakes up to press the determination switch 1b. The central control circuit 20 monitors time. In order to prevent the player from omitting to input the mode, when it is usual bedtime or it is the usual hour of rising, the central control circuit 20 causes the buzzer 3 to make alarm sound such as a peep, thereby urging the player to input the sleep information SD. This alarm sound continues for a period of time of the average value "±α" of time when the determination switch 1b is pressed, or a period of time of the expected bedtime and the expected hour of rising "±α" (for example, "α"=20 minutes) which are set in the initial setting until the sleep information SD is input. The alarm function of the hour of rising can also be used as an alarm clock (Step S2).

The mode "meal" is a mode for inputting the information FD of a food which the player wants to eat or a food which the player will eat. The food information FD is input such that a food is selectively designated from the food list displayed on the liquid-crystal display unit 2. In the displayed food list, foods are classified by types, and quantities of intake calories for foods are set in advance. When the mode "meal" is selected, as shown in FIG. 6A, a food list FD1 showing the types of foods (rough classification) is displayed on the liquid-crystal display unit 2. When a type of food (1 to n) is selected from the food list FD1, as shown in FIG. 6B, a food list FD1n showing foods and intake calories belonging to the type is displayed. The example shown in FIG. 6B shows an example wherein the classification of "rice" is selected in the food list FD1 in FIG. 6A. Foods which the player has eaten are selected from the food list FD11. The order of candidates of the foods displayed in the food lists FD1 and FD11 is displayed in such a manner that priority is given to a food which is selected many times, i.e., a food which is eaten many times. The food list is scrolled according to the operation of the selection switch 1a. In this embodiment, one operation of the determination switch 1b corresponds to one unit of a food or a drink. For example, when two bowls of rice are eaten, the determination switch 1b is pressed again to designate them. When half of a bowl of rise is eaten, or when a food which is not on the food list is eaten, "others" is selected, and the determination switch 1b is pressed to input an intake calorie in units of, e.g., 50 Kcal (Step S3).

The mode "exercise" is a mode for inputting the exercise information MD by using the operation unit 1. In this embodiment, a quantity of exercise by ordinary walking is designed to be automatically measured, and information obtained when other relatively heavy exercise is selectively designated from an exercise to be input. When the player does not hold the health management device, information is input from the exercise list. As the exercise information, a quantity of consumption calorie consumed by performing the exercise for a predetermined period of time is set in advance every weight and every type of exercise. When the exercise information is to be displayed on the liquid-crystal display unit 2, an exercise list depending on the weight of the player is displayed. FIG. 7 shows an exercise list MD1 displayed when a current weight is 50 Kg. When the mode "exercise" is selected, as shown in FIG. 7, a list of types of exercise and consumption calories per unit time is displayed as the exercise list MD1. The order of candidates of the exercise displayed in the exercise list MD1 is displayed in such a manner that priority is given to exercise which is selected many times, i.e., an exercise which is performed many times, as in the food list. The exercise list is scrolled according to the operation of the selection switch 1a. In this embodiment, one operation of the determination switch 1b corresponds to one unit (e.g., 10 minutes) of a quantity of exercise. For example, when rapid walking is performed for 30 minutes, "rapid walking" is selected, and the determination switch 1b is pressed three times to designate the exercise. When exercise which is not on the exercise list is performed, "others" is selected, and the determination switch 1b is pressed to input a consumption calorie in units of, e.g., 50 Kcal (Step S4).

When the food information FD is input in Step S3, the intake calorie calculation unit 22 calculates the sum of intake calories of the selected foods, and the sum of calories is added to the intake calorie of the day to be stored (Step S5). When the exercise information MD is input in Step S4, the consumption calorie calculation unit 23 calculates a consumption calorie corresponding to a measured quantity of exercise or a quantity of exercise selectively designated from the exercise list, and the consumption calorie is added to the consumption calorie of the day to be stored. In this embodiment, as an exercise quantity measurer, the step count detector 10 consisting of a vibration sensor or the like is incorporated. A walking distance is calculated on the basis of a detection signal from the step count detector 10, a detection interval, and personal information (height), so that a calorie consumed by walking is calculated on the basis of the walking distance.

As calories consumed by a person, a "basal metabolic rate (rest-state metabolic rate)" required to keep the life even in a rest state, an "active energy rate" consumed when the person moves his/her body, and food-inductive thermogenesis rate" consumed when food is absorbed are known. It is said that a general person who performs some exercise has the following ratio. That is, in general, the basal metabolic rate is 60%, the active energy rate is 30%, and the food-inductive thermogenesis rate is 10%. In this invention, the active energy rate is calculated by the above method, and the basal metabolic rate is calculated on the basis of a metabolic rate ((calorie consumed in sleeping)*(weight rate)) in a sleeping time calculated by the sleep information SD and a metabolic rate in a time of a relatively rest state obtained by subtracting an exercise time and the sleeping time from 24 hours. The "food-inductive thermogenesis rate" is calculated on the basis of a standard value depending on the number of meals. These consumption energies (consumption calories) are added to the calories consumed by exercise of the day to be stored (Step S6).

Analysis of a calorie balance (to be described later), simulation of a diet effect, and determination of a health condition are performed at predetermined times or every predetermined period. In the calorie balance analyzer 24, an elapsed time from reference time is checked to determined whether one day has elapsed or not (Step S7). If one day has elapsed, the recorded data of an intake calorie Ca and a consumption calorie Cb of the day calculated in Steps S5 and S6 is loaded to check a calorie balance (Step S8). In this embodiment, if intake calorie Ca>consumption calorie Cb, "excessive calorie" is determined, and the difference (Ca−Cb) is calculated to update a weight-gain variable X1. If intake calorie Ca<consumption calorie Cb, "lack of calorie" is determined, and the difference (Ca−Cb) is calculated to update a weight-loss variable X2. However, a variable Xa (integration value of Ca−Cb) of (quantity of loss of weight)/(quantity of gain in weight)=X1=X2. In the process (to be described later), the quantity of loss of weight and the quantity of gain in weight are determined by the sign and absolute value of the variable Xa (Steps S9 and S10).

In the health condition determination unit 26, the degrees of health elements such as overeating, unbalanced eating, and a lack of exercise are calculated on the basis of the food information FD, the exercise information MD, and the personal information PD, and the degree of health is determined on the basis of the sum of the degrees of health elements. Overeating is checked by calculating the difference between an intake calorie per day and a standard value (standard intake calorie depending on sex, height, and the like). A lack of exercise is checked such that the degree of lack of exercise is determined by calculating the difference an average value of a quantity of exercise (consumption calorie by exercise) in a predetermined period or a quantity of exercise of the day and a standard value (standard quantity of exercise depending on age, sex, weight, and the like). Unbalanced eating is checked by checking whether the same type of food is continuously eaten for a predetermined period. For example, it is checked on the basis of the recorded information of eaten foods whether the same food is eaten one day before (Step S11). If the same food is eaten, an unbalanced eating counter is updated by "+1" (Step S12). If a different food is eaten, the unbalanced eating counter is cleared (Step S13). If the value of the unbalanced eating counter is a threshold value or more, unbalanced eating is determined. Information of nutrition elements is set in correspondence with the types of foods, and a nutrition balance analyzing means for analyzing the nutrition balance of a selectively designated food is arranged. On the basis of the information of accumulated and recorded nutrition balance, the display character may be changed in action, proportion, color, and the like to display the state of the nutrition balance.

A simulation method in the diet effect simulation unit 25 will be described below.

Here, factors in corpulence or over-thinning, in particular, factors in corpulence will be considered below. Although there are various factors in corpulence, it is understood that an environmental influence such as "overeating", "erroneous way of eating", or "lack of exercise" is larger than a hereditary influence by a gene. The "overeating" means that an intake calorie higher than a consumption calorie. An excessive calorie is stored as fat to cause corpulence. In addition, if overeating is not performed, an "erroneous way of eating" causes corpulence. For example, when two meals are taken per day, or when a large quantity of food is eaten in one meal, nutrition is easily absorbed. For this reason, excessive calories are caused, and body fat is excessively stored. In addition, the function of digestive organs is active at night, and foods are easily absorbed from the stomach and intestines. It is said that an amount of secreted insulin which operates to promote synthesis of fat increases. The energy of food eaten is easily converted into fat at night than at day. Furthermore, "lack of exercise" is regarded as an important factor in corpulence because the "lack of exercise" not only decreases consumption energy but also causes abnormal metabolism which accumulates fat. It is said that "lack of exercise" is the most important main factor in corpulence.

In the present invention, these environmental factors are used as parameters to simulate a diet effect. As the factor according to "overeating", the variable Xa of (quantity of loss of weight)/(quantity of gain in weight) calculated in Steps S9 and S10 is used. A factor according to "erroneous way of eating" is obtained such that the degree of error of the way of eating is calculated on the basis of, e.g., the number of meals per day, an intake calorie per meal, and a time zone of meal, and the variable Xa of (quantity of loss of weight)/(quantity of gain in weight) is corrected by using a non-digestion calorie as a calorie depending on the degree of error. A factor according to "lack of exercise" is obtained such that the variable Xa of (quantity of loss of weight)/(quantity of gain in weight) is corrected by using a calorie depending on the degree of lack of exercise calculated by the health condition determination unit 26 as a non-digestion calorie. A weight WN (Kg) calculated by the following equation (1) is set as a standard weight, and a quantity of loss of weight and a quantity of gain in weight are determined by the sign and absolute value of the variable Xa. The moving image display controller 27 changes the character in proportion or action depending on the quantities to display a diet effect.

$$WN = 22 * T^2 \tag{1}$$

Where T height of player, and 22 is the Kaup Index.

In this embodiment, if quantity of gain in weight>threshold value Sa, the character in FIG. 5A is switched to a character which becomes fat by one stage to display the switched character (Steps S14 and S15). If quantity of loss of weight>threshold value Sb, the character in FIG. 5A is switched to a character which becomes slim by one stage to display the switched character (Steps S16 and S17). The rate of a change in weight depends on the type of a character. For example, when a personified character is used, the rate of a change in proportion is equal to the rate of a change in proportion of a real person (e.g., the proportions are not changed for a short period such as 1 or 2 days, and the proportions are changed in unit of weeks or months). When a pseudo creature character is used, the rate of a change in proportion is several times the rate of a change in proportion of a person. In addition, when a current weight becomes a target weight or a standard weight, the feeling of achievement is expressed by the gesture or expression of the character.

A control of main actions of a character will be described below. The proportions and actions of the character are controlled on the basis of variable parameters such as a quantity of food intake, a quantity of exercise, a weight, bedtime, the hour of rising, and the degree of unbalanced eating. A character displayed on the liquid-crystal display unit 2 always do something on the screen. The character is programmed such that the action, proportions, color, and sound change depending on the behavior of a player, and the character is transformed.

Figure 5B:
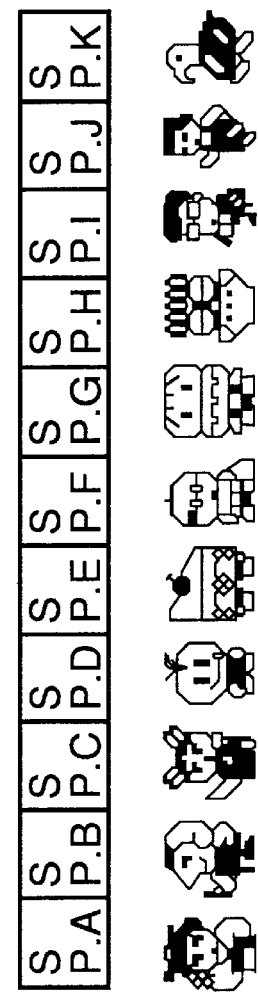

A control of a character action based on the food information FD will be described below. When an eaten food is selectively designated, the character action is switched to an eating action to display the eating action. At this time, it is checked on the basis of the sum of intake calories of one meal and personal information (age, height, and sex) whether overeating is executed or not. If overeating is executed, a manner in which the character becomes sick and vomits out is displayed. If the player does not eat anything for several hours, the character makes a hungry gesture. If the intake calories of the day are over, the device makes alarm sound such as a peep. In addition, it is checked whether the count value of the unbalanced eating counter obtained in Steps S11 to S13 exceeds the threshold value Sc (Step S18). If YES in Step S18, unbalanced eating is determined, and the character transforms (mutation) its figure to warn the player of the unbalanced eating. As the character after mutation, as shown in FIG. 5B, a plurality of characters (SP. A–K) are set. The character after mutation is determined depending on the degree of unbalanced eating or at random (Step S19).

A control of a character action mainly based on the information of a quantity of exercise will be described below. When the exercise quantity measurer (step count detector) 10 operates, the character action is displayed according to the exercise. In this embodiment, a waking action is changed depending on the count value and detection interval of the step count detector 10 to display the walking action. At this time, the waling action is changed depending on a current weight such that a fat character slowly walks, a slim character walks with jumps, and a standard character lightly and smartly walks. If the exercise information MD is input by selection of the exercise list, a walking action is changed in the same manner as described above to be displayed for the time of the exercise information MD. On the basis of the quantity of exercise and personal information (age, sex, and weight), it is checked whether over-exercise is executed or not. If over-exercise is executed, the character makes a tired action. In this manner, the action of the character is changed depending on the quantity of exercise.

A control of a character action based on information about bedtime and the hour of rising will be described below. When a mode "sleeping" is selected, and the determination switch 1b is pressed, a sleeping manner of the character and a sleeping state are displayed. When a mode "rising" is selected, and the determination switch 1b is pressed, the character rises up to set an ordinary action state.

In an ordinary state, the gesture or expression of the character is changed depending on the degree of health obtained by the health condition determination unit 26 or the food intake state. For example, when the best weight and the best degree of health are achieved, the character makes the cutest action, and a face color, generated sound, or the like is changed depending on the degree of health.

As described above, according to the present invention, a function of displaying a diet effect and the health condition with a moving image like a game is arranged. A situation observation function of displaying a current situation and progress by a numeral value, a graph, or the like is also arranged. The mode "situation observation" is a mode for seeing a diet effect or a health condition. When this mode is selected, the menu of an observation command (exercise, quantity of intake calorie, weight, degree of health, see) is displayed on the liquid-crystal display unit 2. The "exercise" is a command for collating the integration value (kilometers that the player walks up to this) of a walking distance of the day and a quantity of consumption calorie, and the "quantity of intake calorie" is a command for collating a quantity of intake calorie of each meal of the day and a total quantity of intake. The "weight" is a command for collating a current weight, a standard weight, a quantity of loss of weight (gain in weight) from the start point, and the "degree of health" is a command for collating the current degree of health (score 1 to score 10) obtained by the health condition determination unit 26. The "see" is a command for making it possible to observe an enlarged image. When this command is selected, an image is enlarged, and the image can be scrolled and displayed, thereby showing the enlarged image.

Figure 8:
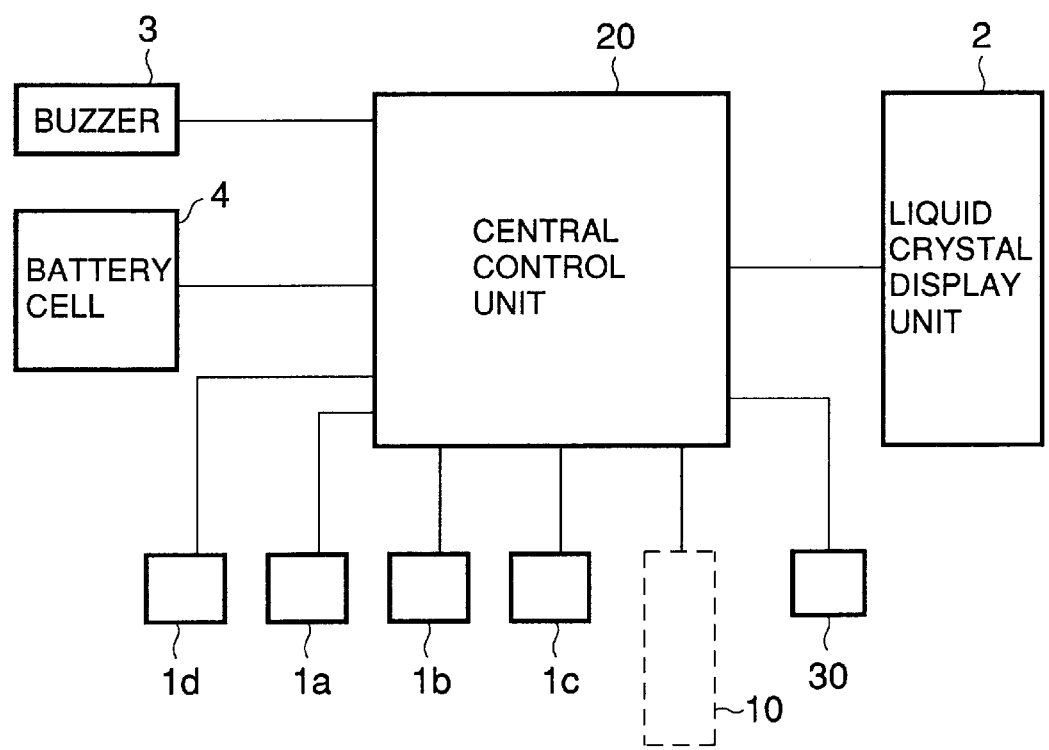
FIG. 8 is a block diagram showing another hardware arrangement of the device according to the present invention.

FIG. 8 is a block diagram showing another hardware arrangement of a portable health management device according to the present invention. The health management device comprises a measurement information input means 30 constituted by a communication means, an input terminal, or the like. The health management device is designed to receive information from an external device having a function of measuring a quantity of exercise and to make it possible to calculate a quantity of exercise (consumption calorie or the like) on the basis of the measurement information. For example, when a measurement information output means (communication means, an output terminal, or the like) is arranged on an indoor athletic tool having a function of measuring a quantity of running or a quantity of exercise by a bicycle, various types of exercise information are input from the external device, and calories consumed by various exercises can be automatically calculated.

In the above embodiment, although a character appearing at the first has been described as a fixed character (character having standard proportions), an appearing character may be determined depending on the age, sex, and weight which are registered. In addition, a plurality of personified characters and a plurality of pseudo creature characters are prepared, so that a player may select a desired character.

As has been described above, according to the present invention, the state of gain in weight or loss of weight is simulated on the basis of the information of a quantity of food and a quantity of exercise, the behavior of a player, a diet effect, the health condition, and the like are reflected on the behavior or the like of a character serving as the other self to express them with a moving image. For this reason, an improvement of an eating habit or coping with a lack of exercise can be pleasantly achieved with the feeling of game, and diet can be performed with playing a game. In addition, the behavior of a player immediately appears as the action of the other self, and calorie balance, overeating, unbalanced eating, lack of exercise, and a health condition are displayed. Therefore, "overeating", "erroneous way of eating", "lack of exercise", and the like can be easily recognized, and the health management device can be made good use of health management.

What is claimed is:

1. A health management device comprising:

exercise quantity measurement means for measuring a quantity of exercise;

intake calorie calculation means for calculating an intake calorie on the basis of input information of meals, including the types and quantities of foods;

consumption calorie calculation means for calculating, on the basis of a information of a quantity of exercise measured by said exercise quantity measurement means, the calories consumed by the exercise;

calorie balance analysis means for analyzing a calorie balance on the basis of the calculation results of the intake calories and the consumption calories;

diet effect simulation means for simulating a diet effect on the basis of the information of the analyzed calorie balance and personal information; and moving image display control means for changing a display character to display the diet effect with a moving image.

2. A health management device according to claim 1, further comprising a step count detector for detecting the number of steps walked by a holder, wherein said exercise quantity measurement means measures the quantity of walking exercise on the basis of detected information of said step count detector and the personal information.

3. The health management device according to claim 1, wherein said exercise quantity measurement means measures the quantity of exercise of the exercise on the basis of input information from an external device having the function of measuring the quantity of exercise.

4. The health management device according to claim 1, wherein unbalanced eating is checked on the basis of recorded data of the information of meals, and the character is changed depending on state of unbalanced eating.

5. The health management device according to claim 1, comprising health condition determination means for determining a health condition on the basis of an analysis result of the calorie balance, the information of the meals, information on the quantity of exercise and the personal information, wherein said moving image display control means changes the character depending on the determined result of said health condition determination means to display a health condition with a moving image.

6. The health management device according to claim 1, comprising nutrition balance analysis means for analyzing the nutritional balance of the input foods on the basis of information of the nutritional elements set in correspondence with the types of foods, wherein the character is changed on the basis of the analyzed result of the nutritional balance.

7. The health management device according to claim 1, wherein said consumption calorie calculation means calculates the degree of error of the manner of eating on the basis of the number of meals per day, the quantity of intake calories of one meal, and a time zone of the meals based on the information of the meals; corrects the digestion calorie by using a calories depending on the degree of error as a non-digestion calorie, and calculates time in a rest state in which no exercise is executed on the basis of the information of the quantity of exercise, so that the digestion calorie is corrected by using a basal metabolic rate depending on the time as a digestion calorie.

8. The health management device according to claim 1, wherein said health management device is a portable compact game machine in which a step count detector for detecting the number of steps walked by a holder is provided, a character obtained by personifying the holder as a hero is set to be a character displayed by said moving image display control means, and the story of the game is developed depending on the behavior of the holder determined on the basis of detected information of said step count detector and the information on the meal.

9. The health management device according to claim 1, wherein said personal information means includes height and weight measurements.

10. The health management device according to claim 1, wherein said moving image display controller changes the action of the character depending on the quantity of exercise.

11. The health management device according to claim 1, wherein said input information of meal is selectively designated from the food list displayed on the display unit.

12. The health management device according to claim 1, comprising display situation means which displays the current situation and the progress being made by means of a graph.

13. The health management device according to claim 5, wherein said display character is changed in action, proportion, and color to display said health condition.

14. The health management device according to claim 1, wherein this kind of said character is determined based on the input of said personal information.

15. The health management device according to claim 1, wherein this kind of said character is selected from a plurality of characters.

16. The health management device according to claim 1, wherein said character is a personified character.

17. The health management device according to claim 1, wherein said character is a pseudo creature character.

* * * * *